(12) United States Patent
Ralph et al.

(10) Patent No.: US 6,527,806 B2
(45) Date of Patent: Mar. 4, 2003

(54) INTERVERTEBRAL SPACER DEVICE HAVING A SPIRAL WAVE WASHER FORCE RESTORING ELEMENT

(75) Inventors: James D. Ralph, Oakland, NJ (US); Steven Tatar, Montvale, NJ (US); Joseph P. Errico, Far Hills, NJ (US)

(73) Assignee: Third Millennium Engineering, LLC, Summit, NJ (US)

( * ) Notice: Subject to any disclaimer, the term of this patent is extended or adjusted under 35 U.S.C. 154(b) by 0 days.

(21) Appl. No.: 09/906,118

(22) Filed: Jul. 16, 2001

(65) Prior Publication Data

US 2003/0014111 A1 Jan. 16, 2003

(51) Int. Cl.$^7$ .................................................. A61F 2/44
(52) U.S. Cl. .............................. 623/17.16; 623/17.13; 623/17.11
(58) Field of Search .......................... 623/16.11, 17.11, 623/17.12, 17.13, 17.14, 17.15, 17.16; 606/72, 73, 86

(56) References Cited

U.S. PATENT DOCUMENTS

| | | | |
|---|---|---|---|
| 5,458,642 A | 10/1995 | Beer et al. | |
| 5,556,431 A | 9/1996 | Buttner-Janz | |
| 5,562,738 A | 10/1996 | Boyd et al. | |
| 5,674,296 A | 10/1997 | Bryan et al. | |
| 5,676,701 A | 10/1997 | Yuan et al. | |
| 5,676,702 A | 10/1997 | Ratron | |
| 5,683,465 A | 11/1997 | Shinn et al. | |
| 5,755,796 A | 5/1998 | Ibo et al. | |
| 5,827,328 A | 10/1998 | Butterman | |
| 5,865,846 A | 2/1999 | Bryan et al. | |
| 5,888,226 A | 3/1999 | Rogozinski | |
| 5,895,428 A | 4/1999 | Berry | |
| 5,899,941 A | 5/1999 | Nishijima | |
| 5,989,291 A | 11/1999 | Ralph et al. | |
| 6,001,130 A | 12/1999 | Bryan et al. | |
| 6,019,792 A | 2/2000 | Cauthen | |
| 6,039,763 A | 3/2000 | Shelokov | |
| 6,063,121 A | 5/2000 | Xavier et al. | |
| 6,113,637 A | 9/2000 | Gill et al. | |
| 6,136,031 A | 10/2000 | Middleton | |
| 6,146,421 A | 11/2000 | Gordon et al. | |
| 6,156,067 A | 12/2000 | Bryan et al. | |
| 6,179,874 B1 | 1/2001 | Cauthen | |
| 6,228,118 B1 | 5/2001 | Gordon | |
| 6,375,682 B1 * | 4/2002 | Fleischmann et al. | ... 623/17.12 |

* cited by examiner

*Primary Examiner*—Michael A. Brown
*Assistant Examiner*—Benjamin K. Koo
(74) *Attorney, Agent, or Firm*—Joseph P. Errico, Esq.; Timothy J. Bortree, Esq.

(57) ABSTRACT

An intervertebral spacer device having a pair of opposing plates for seating against opposing vertebral bone surfaces, separated by at least one force restoring element. The preferred force restoring mechanism is a spiral-shaped radially diminishing amplitude wave washer.

7 Claims, 3 Drawing Sheets

INTERVERTEBRAL SPACER DEVICE HAVING A SPIRAL WAVE WASHER FORCE RESTORING ELEMENT

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device which utilizes a wave washer as a force restoring element.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer which stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space which does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of a spring mechanism. In particular, this spring mechanism initially provides a weak restoring force when a compressive load is applied to the plates, but which restoring force becomes increasingly stronger as the compressive load increases. The spring mechanism may also permit limited rotation of the two plates relative to one another. While there are a wide variety of embodiments contemplated, the principle embodiment described herein includes a spiral-shaped wave washer having a radially diminishing amplitude.

More particularly, with respect to the base plates, which are similar in all embodiments, as the assembly is to be positioned between the facing surfaces of adjacent vertebral bodies, and as such need to have substantially flat external surfaces which seat against the opposing bone surfaces. Inasmuch as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to the bone, the upper and lower plates may each include outwardly directed spikes which penetrate the bone surface and mechanically hold the plates in place. Alternatively, the base plates may be coupleable to other securing means for holding the present invention in place.

It is further anticipated that the plates may include a porous coating into which the bone of the vertebral body can grow. (Note that this limited fusion of the bone to the base plate does not extend across the intervertebral space.)

Between the base plates, on the exterior of the device, there is included a circumferential wall which is resilient and which simply prevents vessels and tissues from growing into the interior of the device. This resilient wall may comprise a porous fabric or a semi-impermiable elastomeric material, and serves a similar purpose to the naturally occurring annulus material which surrounds the cartilage of the intervertebral disc, which the present invention is designed to replace when conditions warrant. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials which could be utilized herein may be found in the field of orthopaedic in conjunction with ligament and tendon repair. It is anticipated that future developments in this area will produce materials which are compatible for use with this invention, the breadth of which shall not be limited by the choice of such a material.

As introduced above, the internal structure of the present invention comprises a force restoring member, which provides a restoring force of variable strength when compressed. More particularly, it is desirable that the restoring force, which is directed outward against the opposing plates, initially be lax, becoming more stiff as the applied compressive load becomes more intense. This feature imbues the spring mechanism with substantially better anatomical performance characteristics than other spring mechanisms previously contemplated.

In addition, in certain preferred embodiments, the restoring force providing subassembly does not substantially interfere with the rotation of the opposing plates relative to one another. Alternatively, the base plates may be selectively securable to the washer in such a way that it substantially inhibit any rotation of the plates. These alternate rotational capabilities, which are both described hereinbelow, do not materially affect the performance of the spring mechanism.

As further mentioned above, the force restoring member comprises at least one spiral-shaped wave washer having a radially diminishing amplitude. More particularly, wave washers resemble simple round washers which comprise a flat round ring, except that band of material which forms the washer rises and falls in a wave-like undulation around its circumferential edge. Stated alternatively, a standard washer is a relatively planar ring-shaped object, confined to the x-y plane. In the present invention, the wave washer is spiral-shaped in that it sweeps out an angle greater than 360 degrees and has an ever increasing radius. In the case of the spiral-shaped wave washer of the present invention, the amplitude of the undulations also decreases in the radial direction. The wave washer, thereby, takes on the appearance of a spiral galaxy, having a thicker central disc, and a flatter edge.

Inasmuch as the restoring force of a wave washer is proportional to the elastic properties of the material and the amount of material being deformed, the magnitude of the restoring force provided by the wave washer may be modified by altering the thickness of the material in its radial extent, or in its z-axis. In the case of the spiral-shaped wave washer of radially diminishing amplitude, a varying restoring force is realized as the number of spirals of the spring which are engaged increases (as the base plates compress toward each other the spirals of lesser amplitude are progressively defectively engaged). (For the purposes of this description, the top and the bottom of a wave washer shall be defined as the planes defined by the highest and lowest points of the circumferential undulations, respectively.)

As a compressive load is applied by a pair of plates against the top and bottom of a wave washer, the forces are first directed against the arches of the undulating waves at the center of the spiral, and are increasingly directed against the arches of the outer "rings". These loads are also translated into a hoop stress which tends to radially expand the spirals of the washer in its x-y plane. This force of deflection against the arches, and the hoop stress in the radial direction, are counterbalanced by the material strength of the washer. The strain of the material causes a deflection in the height of the washer and a slight radial expansion. Stated equivalently, a wave washer responds to a compressive load by deflecting compressively in z-axis, radially, and circumferentially.

In general, the spiral wave washer is one of the strongest configurations for a spring, and is highly suitable for use as a restoring force providing subassembly for use in an intervertebral spacer element which must endure considerable cyclical loading in an active human adult.

In a preferred embodiment of the present invention, a simple screw locks one of the ends of the washer to the base plate.

Finally, inasmuch as the human body has a tendency to produce fibrous tissues in perceived voids, such as may be found within the interior of the present invention, and such fibrous tissues may interfere with the stable and/or predicted functioning of the device, preferred embodiments of the present invention may be filled with a highly resilient elastomeric material. The material itself should be highly biologically inert, and should not substantially interfere with the restoring forces provided by the spring mechanisms therein. Suitable materials may include hydrophilic monomers such as are used in contact lenses. Alternative materials include silicone jellies and synthetic collagens such as have been used in cosmetic applications. As with the exterior circumferential wall, which was described above as having a variety of suitable alternative materials, it is anticipated that future research will produce alternatives to the materials described herein, and that the future existence of such materials which may be used in conjunction with the present invention shall not limit the breadth thereof.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
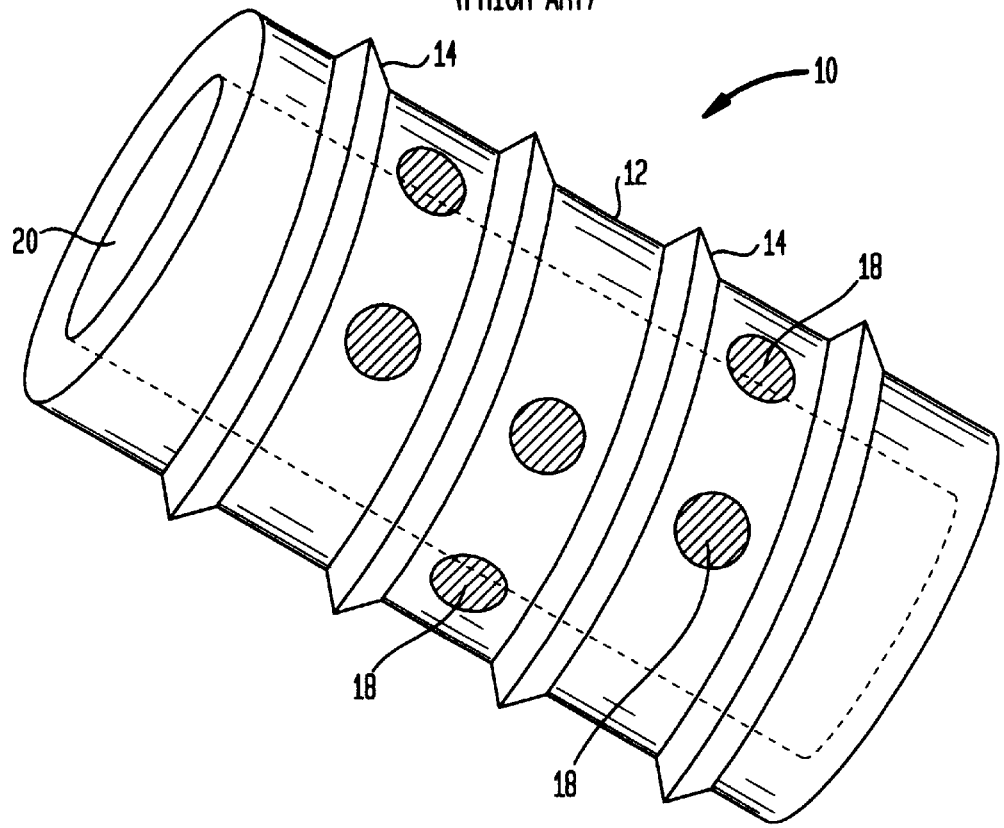
FIG. 1 is a side perspective view of an interbody fusion device of the prior art.
Figure 2:
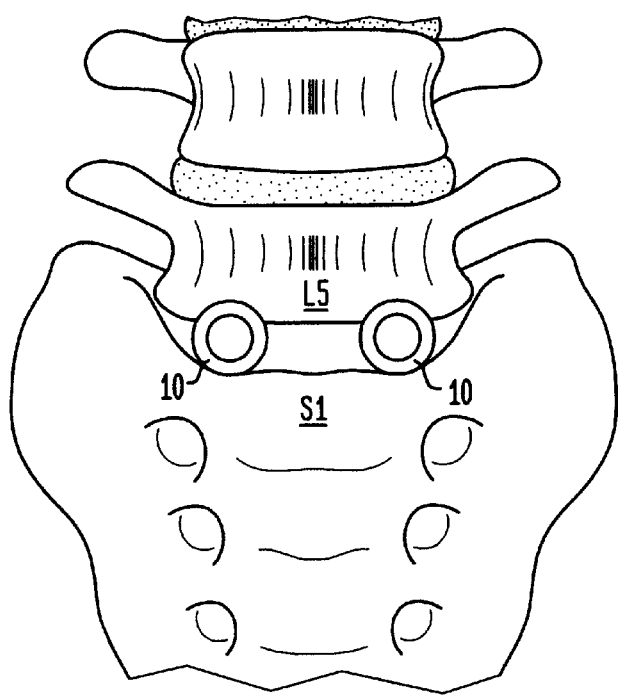
FIG. 2 is a front view of the anterior portion of the lumbo-sacral region of a human spine, into which a pair of interbody fusion devices of the type shown in FIG. 1 have been implanted.
Figure 3A:
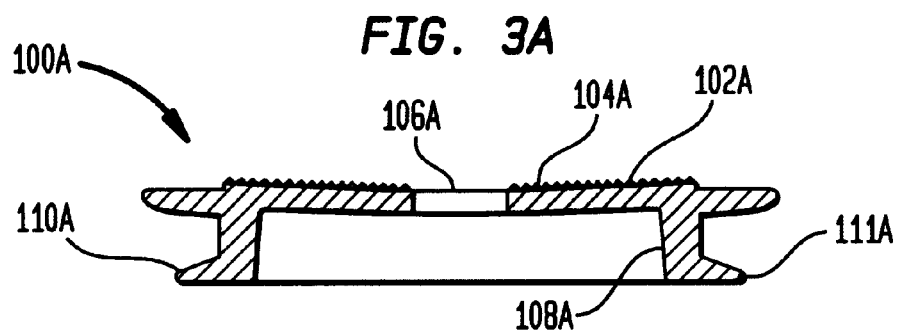
FIGS. 3a and 3b are side cross-section views of the upper and lower opposing plates of the present invention.
Figure 3B:
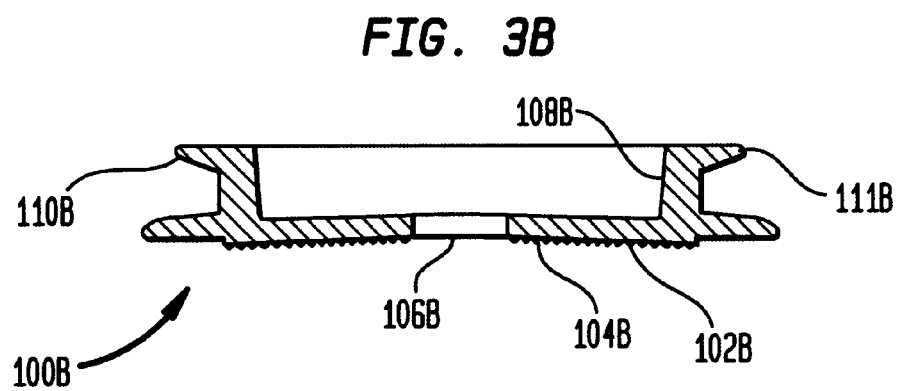

Referring now to FIGS. 3a and 3b, side cross-section views of the top and bottom plate members 100a 100b of a first embodiment of the present invention is shown. More particularly, in this embodiment, the upper and lower plates 100a,100b are substantially identical. As the device is designed to be positioned between the facing surfaces of adjacent vertebral bodies, the plates include substantially flat surface portions 102a,102b which seat against the opposing bone surfaces. In addition, the plates are to mate with the bone surfaces in such a way as to not rotate relative thereto. It is, therefore, preferred that the plates should include a porous coating 104a,104b into which the bone of the vertebral body can grow. (Note that this limited fusion of the bone to the base plate does not extend across the intervertebral space.) An additional threaded hole 106a,106b is provided in each plate such that the interior of the device may be readily accessed if a need should arise.

The plates 100a,100b further include a circumferential flange 108a,108b. The flange 108a,108b may be offset with respect to the front 110a,110b and rear 111a,111b orientation of the overall assembly. More particularly, the offset nature of the flanges 108a,108b is exhibited in the non-symmetric appearance of each flange as it circumscribes the corresponding plate 100a,100b. By this it is meant that the portion of the flange 108a,108b which corresponds to the rear 111a,111b of the device is shorter than the portion corresponding to the front 110a,110b of the device.

Figure 4:
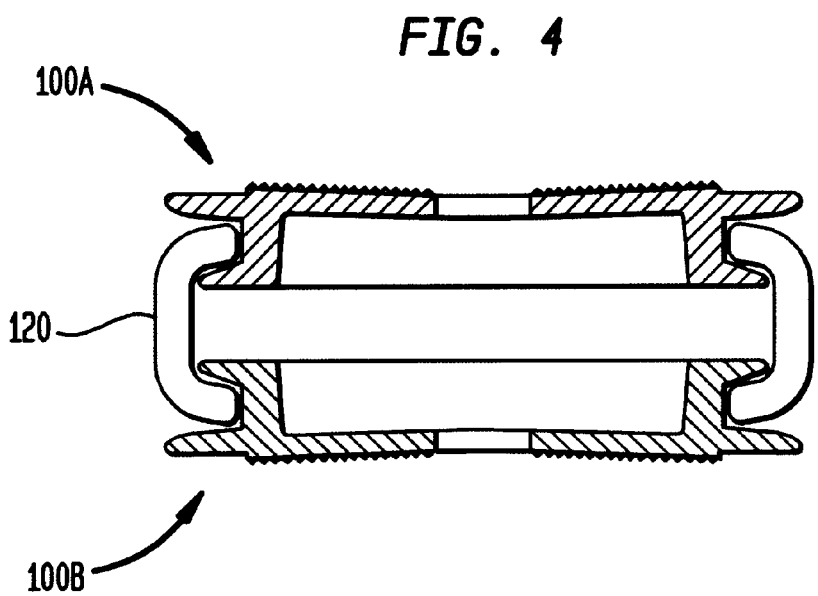
FIG. 4 is a side cross-section view of the opposing plates in association with one another, wherein an exterior skirt is included.

Referring now to FIG. 4, a partially assembled embodiment of the present invention is provided in a side cross-section view, wherein the upper and lower plates 100a,100b illustrated in FIGS. 3a and 3b are joined by means of a circumferential wall 120. More particularly, between the base plates 100a,100b, on the exterior of the device, there is included a circumferential wall 120 which is resilient and which is provided to prevents vessels and tissues from entering within the interior of the device. It is preferred that the resilient wall 120 comprise a porous fabric or a semi-impermiable elastomeric material. The wall 120 is further designs to couple to the flanges 108a,108b of the corresponding plates 100a,100b.

Figure 5:
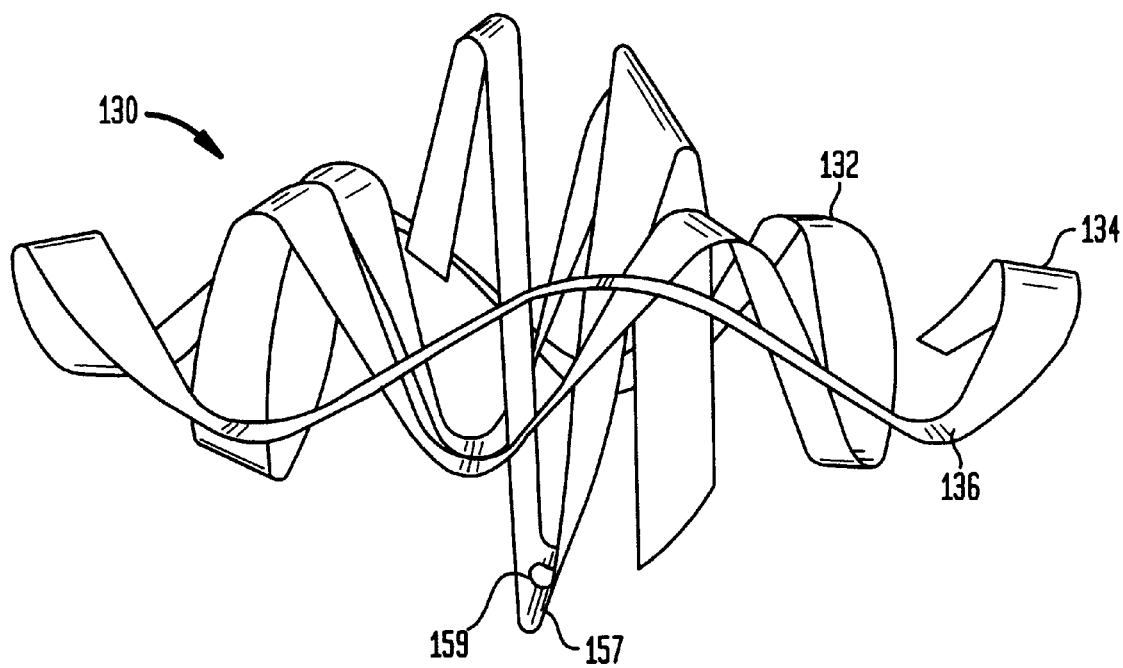
FIG. 5 is a side perspective view of a spiral-shaped wave washer having a radially diminishing amplitude of the type which is utilized in conjunction with the present invention.

Referring now to FIG. 5, the spiral-shaped radially diminishing amplitude force restoring element which comprises a component of the present invention is provided in a perspective view. More particularly, a wave washer 130 is so named inasmuch as it is comprised of a curved band of material (a titanium alloy or stainless steel is preferable, although other suitable surgical materials may be found to function adequately), which band rises and falls in an undulating wave-like conformation 132. In the case of a spiral wave washer, the curvature begins in a tightly wound center and expands outward as a spiral. The periodic arches 134 and valleys 136 provide the wave. In the spiral wave washer of the present invention, amplitude of the waves at the center of the washer are greater than the amplitude at the outer regions, such that a compressive load applied to the washer is initially borne by the central, larger waves, and only as the washer is heavily loaded do the outer waves become engaged.

More particularly, the restoring force of a wave washer of the type illustrated in FIG. 5 is proportional to the elastic properties of the material. As a compressive load is applied to the washer by the opposing plates, the forces are directed down onto the arches 134 and up against the valleys 136. The first arches and valleys to be engaged provide a limited opposing (i.e. restoring) force. As the load continues to increase, a larger portion of the spiral is engaged, thereby causing the restoring force to climb substantially. This is a much more anatomically accurate response.

As the loading is applied, a significant fraction of these compressive forces are immediately translated into quasi-hoop stresses which radially expanding the washer. This hoop stress is also counterbalanced by the material strength of the washer. Unlike a continuous ring-shaped washer (which has a very high stress to deflection ratio), a spiral-shaped wave washer deflects circumferentially (this is characteristic of a much lower stress to deflection ratio). However, the increased number of waves which must be engaged as the deflection increases provides greater resistance as the washer is heavily compressed.

Figure 6:
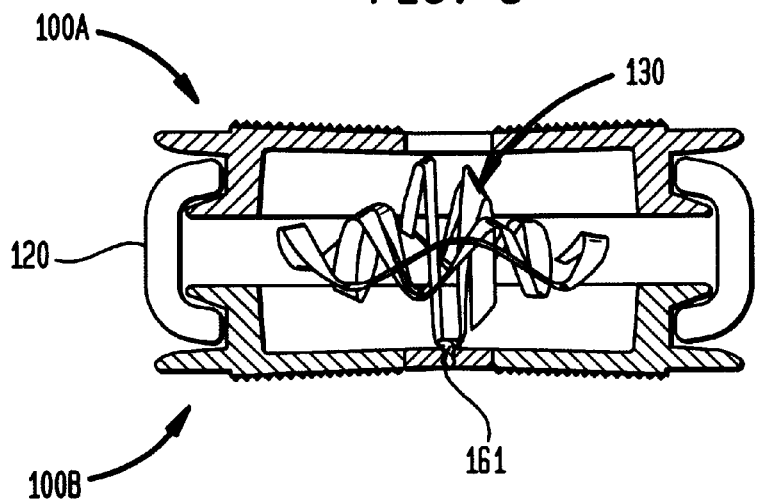
FIG. 6 is a side cross-section view of an embodiment of the present invention.

Referring now to FIGS. 3, 5 and 6, the means for securing the spiral-shaped radially diminishing amplitude wave washer is now described. The innermost end 157 of the spiral band of the wave washer includes a threaded hole 159 which aligns with the threaded hole 106a or 106b in the base plate to which it is to be secured. A screw 161 shown in FIG. 6 secures the washer to the base plate through the aligned holes.

Referring now specifically to FIG. 6, an integrated device embodying the principles of the present invention is provided in a side cross-section view. The base plates 100a, 100b are disposed in a spaced apart relationship such that the opposing inner surfaces are approximately parallel and facing one another. A single spiral-shaped radially diminishing amplitude wave washer 130 is disposed between the plates, and retained therein by the circumferential flanges 108a,108b. The spiral-shaped radially diminishing amplitude wave washer 130 is constrained against rotational motion by a screw 161. A flexible circumferential skirt 120 is provided around the entirety of the device, such that the tissue of the patient may not grow into, and thereby cause pain, or inhibit the functionality of the device. It shall be understood that the securing screw does not prevent the plates from rotating relative to one another.

In an alternate embodiment, the spiral wave washer can be secured to both plates (at separate points along its spiral shape) and thereby substantially restrain the plates from rotating relative to one another.

In both embodiments, however, the flexible circumferential skirt 120, which is provided around the entirety of the device will inhibit some rotation, but is principally provided such that the tissue of the patient may not grow into, and thereby cause pain, or inhibit the functionality of the device.

While there have been described and illustrated embodiments of an intervertebral spacer device utilizing a spiral-shaped radially diminishing amplitude wave washer force restoring element, it will be apparent to those skilled in the art that variations and modifications are possible without deviating from the broad spirit and principle of the present invention. The present invention shall, therefore, be limited only to the full scope of the claims allowable in light of the disclosures made herein, and in the parallel reference incorporated herein by reference.

What is claimed is:

1. An intervertebral spacer device comprising:

first and second plate members, said plates being disposed in a spaced apart relationship such that one plate surface of said first plate faces one plate surface of the other plate, said facing surfaces being inner surfaces, and the alternative faces of each plate being outer surfaces; and at least one restoring force providing element disposed between the inner surfaces of said first and second plate members, and disposed such that a compressive load applied to the external faces of said plates is counteracted by said at least one restoring force providing element, said at least one restoring force providing element including at least one spiral-shaped radially diminishing amplitude wave washer.

2. The device as set forth in claim 1, wherein the at least one wave washer further comprises a single spiral-shaped radially diminishing amplitude wave washer.

3. The device as set forth in claim 1, further comprising a flexible circumferential skirt disposed about and between lateral perimeters of said first and second plate members, therein defining an interior volume of said device in which said at least one wave washer is disposed.

4. The device as set forth in claim 3, wherein said flexible circumferential skirt comprises a resilient material.

5. The device as set forth in claim 4, wherein said flexible circumferential skirt is porous.

6. The device as set forth in claim 1, wherein said at least one spiral-shaped radially diminishing amplitude wave washer comprises multiple ones of said washer.

7. The device as set forth in claim 1, wherein at least one of said first and second plate members includes a threaded hole, and wherein said spiral-shaped radially diminishing amplitude wave washer includes a hole, which holes maybe aligned, and wherein said device further includes a screw for securing said spiral-shaped radially diminishing amplitude wave washer to the inner surface of said at least one of said first and second plate members which includes the threaded hole.

* * * * *